US012416631B2

(12) United States Patent
Dahl et al.

(10) Patent No.: US 12,416,631 B2
(45) Date of Patent: Sep. 16, 2025

(54) IMMUNOASSAY-BASED DETERMINATION OF IN-SOLUTION BINDING KINETICS

(71) Applicant: Hoffmann-La Roche Inc., Little Falls, NJ (US)

(72) Inventors: Uwe Dahl, Penzberg (DE); Gregor Jordan, Groebenzell (DE); Roland Staack, Munich (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 18/523,859

(22) Filed: Nov. 29, 2023

(65) Prior Publication Data

US 2024/0102999 A1 Mar. 28, 2024

Related U.S. Application Data

(60) Division of application No. 16/508,254, filed on Jul. 10, 2019, now Pat. No. 11,892,448, which is a continuation of application No. 14/419,984, filed as application No. PCT/EP2013/066265 on Aug. 2, 2013, now abandoned.

(30) Foreign Application Priority Data

Aug. 8, 2012 (EP) ..................................... 12179742

(51) Int. Cl.
G01N 31/00 (2006.01)
G01N 33/15 (2006.01)
G01N 33/53 (2006.01)
G01N 33/557 (2006.01)

(52) U.S. Cl.
CPC ........... *G01N 33/557* (2013.01); *G01N 33/15* (2013.01)

(58) Field of Classification Search
None
See application file for complete search history.

(56) References Cited

U.S. PATENT DOCUMENTS

| | | | |
|---|---|---|---|
| 6,057,160 A | 5/2000 | Silber et al. | |
| 9,797,900 B2 | 10/2017 | Dahl et al. | |
| 11,892,448 B2 * | 2/2024 | Dahl | G01N 33/15 |

FOREIGN PATENT DOCUMENTS

| | | |
|---|---|---|
| CN | 101173923 B1 | 9/2011 |
| WO | 2008/005674 A2 | 1/2008 |
| WO | 2011/038301 A2 | 3/2011 |
| WO | 2011/094445 A1 | 8/2011 |

OTHER PUBLICATIONS

Kuang et al. (Bioanalysis, 2010, 2(6), pp. 1125-1140) (Year: 2010).*
Lee et al. (The AAPS Journal, Vo. 13, No. 1, Mar. 2011, pp. 99-110). (Year: 2011).*
Staack et al. Bioanalysis 4(4), p. 381-395, Feb. 1, 2012. (Year: 2012).*
Azimzadeh, A. et al., "Measurement of affinity of viral monoclonal antibodies by ELISA titration of free antibody in equilibrium mixtures" J Immunol Methods 141(2):199-208 (Aug. 9, 1991).
Clark, S., et al., "Determination of Ligand-Protein Dissociation Constants by Electrospray Mass Spectrometry-Based Diffusion Measurements" Anal Chem 76(23):7077-7083 (Dec. 1, 2004).
European Medicines Agency [EMA] et al., "Guideline on Bioanalytical Method Validation" (EMEA/CHMP/EWP/192217/2009; Rev. 1, Corr.2),:1-23 (Jul. 21, 2011).
European Patent Office, "Communication Pursuant to Article 94(3) EPC. EP Patent Application No. 13745066.4" (EPO Office action),:1-9 (Dec. 3, 2015).
Friguet, B., et al., "Measurements of the True Affinity Constant in Solution of Antigen-Antibody Complexes by Enzyme-Linked Immunosorbent Assay" J Immunol Methods 77(2):305-319 (Mar. 18, 1985).
Japanese Govt. Ministry of Health, Labor and Wealth [MHLW] et al., "Draft Guideline on Bioanalytical Method (Ligand Binding Assay) Validation in Pharmaceutical Development":1-17 (Jan. 24, 2017).
Kuang, B., et al., "Therapeutic monoclonal antibody concentration monitoring: free or total?" Bioanalysis 2(6):1125-1140 (Jun. 1, 2010).
Lee, J. et al., "Bioanalytical Approaches to Quantify 'Total' and 'Free' Therapeutic Antibodies and Their Targets: Technical Challenges and PK/PD Applications Over the Course of Drug Development" AAPS J 13(1):99-110 (Mar. 1, 2011).
Martineau, P., Antibody Engineering "Chapter 41: Affinity Measurements by Competition ELISA" Kontermann, R. and Dubel, S.,, Second edition, Berlin Heidelberg, Germany:Springer-Verlag, Berlin Heidelberg, vol. 1:657-665 ( 2010).
Munson, M., et al., "Counterflow Rejection of Adsorbing Proteins for Characterization of Biomolecular Interactions by Temperature Gradient Focusing" Anal Chem 80(1):172-178 (Jan. 1, 2008).
Nieba, L. et al., "Competition BIAcore for measuring true affinities: large differences from values determined from binding kinetics" Anal Biochem (Articel No. 0067), 234(2):155-165 (Feb. 15, 1996).
Staack, R., et al., "Mathematical simulations for bioanalytical assay development: the (un-)necessity and (im-)possibility of free drug quantification" Bioanalysis 4(4):381-395 (Feb. 1, 2012).

(Continued)

*Primary Examiner* — Lisa V Cook
(74) *Attorney, Agent, or Firm* — GENENTECH, INC.

(57) ABSTRACT

Herein is reported a method for the determination of the binding affinity of a binder and its ligand comprising the step of determining based on the result of an immunoassay the fraction of free binder in a sample comprising binder, ligand and binder-ligand-complexes for at least two different binder:ligand ratios in the sample, and if the determined fraction of free binder is not comparable for all used binder:ligand ratios then the binder:ligand ratio in the sample is lowered and the sample is re-analyzed by the same immunoassay, and calculating based on the fraction of free binder in the previous step the binding affinity for the binder to its ligand.

6 Claims, 11 Drawing Sheets

(56) References Cited

OTHER PUBLICATIONS

US Dept. Health and Human Services—FDA, "Guidance for Industry: Bioanalytical Method Validation" (Draft Guidance), Revision 1(Biopharmaceutics):1-34 (Sep. 1, 2013).
Van Eijkeren, J., et al., "Modelling SPME Data from Kinetic Measurements in Complex Samples" Analyst 129(11):1137-1142 (Nov. 1, 2004).

* cited by examiner

IMMUNOASSAY-BASED DETERMINATION OF IN-SOLUTION BINDING KINETICS

CROSS-REFERENCE TO RELATED APPLICATIONS

This application is a divisional of U.S. patent application Ser. No. 16/508,254, filed Jul. 10, 2019, now U.S. Pat. No. 11,892,448, which is a continuation of U.S. patent application Ser. No. 14/419,984, filed Feb. 6, 2015, now abandoned, which is a national stage entry of International Application No. PCT/EP2013/066265, having an international filing date of Aug. 2, 2013, and which claims benefit to European Patent Application No. 12179742.7, 5 filed Aug. 8, 2012, each of which is incorporated herein by reference in its entirety.

FIELD OF THE INVENTION

Herein is reported an immunoassay-based determination of in-solution binding kinetics in buffer or serum/plasma samples.

Background of the Invention

The pharmacological effect of a systemically acting drug is a function not only of the intrinsic activity of the drug, but also of its absorption, distribution, metabolism, and excretion within the human body. These characteristics are combined under the term "pharmacokinetics." Pharmacokinetics is commonly referred to as the study of the time courses (i.e., kinetics) associated with the dynamic processes of absorption, distribution, metabolism, and excretion of a drug and/or its metabolites within a living organism, and is closely interrelated with the fields of biopharmaceuticals, pharmacology, and therapeutics.

Because the body delays the transport of drug molecules across membranes, dilutes them into various compartments of distribution, transforms them into metabolites, and eventually excretes them, it is often difficult to predict the pharmacological effect of a drug in vivo. Researchers, however, commonly use pharmacokinetic studies as one method to predict the efficacy of a drug at a site of action within the body.

Traditionally, researchers involved with preclinical absorption, distribution, metabolism, and excretion studies have used pharmacokinetic/mathematical models coupled with actual drug concentration data from blood (or serum or plasma) and/or urine, as well as concentration data from various tissues, to characterize the behavior and way of a drug within living organisms.

Having pharmacokinetic information at hand it may be seen (1) whether the drug was poorly absorbed to yield sub-therapeutic circulating levels, or (2) whether the drug experienced pre-systemic metabolism to an inactive metabolite. Such information may also provide guidance for subsequent decisions, such as (1) whether to improve drug absorption by altering the salt form or formulation, (2) whether to investigate the possibility of making prodrugs, or (3) whether to consider a different route of administration.

In addition to the foregoing, pharmacokinetic/mathematical models are also generally considered useful for, among other things: (1) predicting plasma, tissue, and urine drug levels with any dosage regimen; (2) calculating the optimum dosage regimen for an individual patient; (3) estimating the possible accumulation of drugs and/or metabolites; (4) correlating drug concentrations with pharmacologic and toxicological activity (i.e., pharmacodynamics); (5) evaluating differences in the rate or extent of availability between formulations (i.e., bioequivalence); (6) describing how changes in physiology or disease affect the absorption, distribution, and/or elimination of the drug; and (7) explaining drug-drug and food-drug interactions.

Pharmacokinetic absorption, distribution, metabolism, and excretion data has also become an integral part of the pharmacological characterization process of promising new drug candidates.

Thus, an essential part of the drug development process is the characterization of pharmacokinetics (PK) and toxicokinetics (TK) of the drug and the establishment of an understanding of the relationship between the pharmacokinetic and pharmacodynamic (PD) effects (PK/PD). Prerequisite for PK/TK assessment is the availability of reliable bioanalytical methods. In contrast to small molecule drugs which are commonly quantified using liquid chromatography-mass spectrometry (LC-MS) based methods, the bioanalytical gold standard technology for therapeutic proteins is a ligand binding assay (LBA). Besides high sensitivity and high-throughput capabilities, a major advantage of LBAs is the possibility to analyze either total drug concentrations or specifically only ligand binding competent drug molecules ("free drug").

A clear understanding of the capabilities and limitations of a bioanalytical assay used for drug quantification is essential to enable a plausible data interpretation. Prerequisite to determine the free drug concentration is the use of a LBA which enables the analysis of ligand binding competent drug molecules in complex matrix, e.g. by use of a target capture assays. However, the selection of an appropriate assay format alone is not necessarily sufficient for accurate determination of the free drug concentration. Drug and target interact in a reversible non-covalent manner governed by the law of mass action. In addition, LBAs are equally based on reversible non-covalent interaction between the drug/analyte and the assay reagents. Consequently, assay results are easily confounded by any interference in the equilibrium of the binding partners. Such assay interferences have been addressed in the current literature, but not been discussed in detail yet (see e.g. Lee, J. W., et al., AAPS. J. 13 (2011) 99-110, Kuang, B., et al., Bioanal. 2 (2010) 1125-1140).

Standard technology for bioanalysis of therapeutic proteins are ligand binding assays (LBA). A major advantage of LBAs is the possibility to differentiate between total drug and target binding competent drug concentrations. However, the selection of an appropriate assay format alone is not necessarily sufficient for accurate determination of the free drug concentration. Drug, target and assay reagents interact in a reversible non-covalent manner governed by the law of mass action. Consequently, assay results are easily confounded by any interference in the equilibrium of the binding partners. A clear understanding of the possibilities and limitations of an assay is, however, essential to enable a plausible data interpretation (see e.g. Staack, G., et al., Bioanalysis 4 (2012) 381-395).

In WO 2008/005674 methods of analyzing binding interactions are reported. Methods for preparation and use of a Coomassie brilliant blue/protein complex are reported in U.S. Pat. No. 6,057,160. Azimzahdeh, A. and Van Regenmortel, M. H. V., report the measurement of affinity of viral monoclonal antibodies by ELISA titration of free antibody in equilibrium mixtures (J. Immunol. Meth. 141 (1991) 199-208). Lee, J. W., et al. (AAPS J. 13 (2011) 99-110) report bioanalytical approaches to quantify "total" and "free" therapeutic antibodies and their targets. Mathematical simulations for bioanalytical assay development are reported by Staack, R. F., et al. (Bioanalysis 4 (2012) 381-395). In WO 2011/094445 engineered polypeptide agents for targeted broad spectrum influenza neutralization are reported.

SUMMARY OF THE INVENTION

There has been a need for the determination of free drug/binder in a sample comprising a mixture of free drug/binder, target-drug/ligand-drug complexes and free target/ligand.

It has been found that the determination of affinity and binding kinetics ($K_D$, rate constant for on- and off-rate) of a binder and its ligand in buffer or serum/plasma samples can be effected with a very limited/small number of measurements/samples, i.e. one or two (and providing an appropriate calibration). The method is based on the finding that the determination of free binder or free ligand is possible if the determination is performed within the linear/constant plateau range of the curve (at low binder/high ligand concentration no changes in free binder fraction, or likewise at high binder/low ligand concentration no changes in free ligand fraction).

It has been found that the determination of a single (one) value (i.e. e.g. one value for the amount of free binder) is sufficient for the determination of affinity. If a further second value is determined, which is optional, the method also comprises an intrinsic quality control of the determined result. Thus, with the method as reported herein no difficult plot of data points has to be acquired and analyzed. It is even not necessary to perform a best fit of the determined data points.

Determination of binding kinetics is possible with the determination of one value, if the affinity is known.

It has been found that the measurement should be performed with samples with excess of one partner (excess of binder over ligand (high binder:ligand ratio) or excess of ligand over binder (high ligand:binder ratio)).

In one embodiment the excess of one partner is at 10 times. In one embodiment the excess of one partner is at least 40 times. In one embodiment the excess of one partner is at least 100 times.

It has been found that the method as reported herein can be used with a sample comprising serum or plasma.

In the method as reported herein is the concentration of the ligand or binder kept constant while the concentration of the respective other partner (i.e. binder or ligand) is varied.

In one embodiment of the method as reported herein is the concentration of the binder kept constant while the concentration of the ligand is varied.

It has been found that at a low binder:ligand ratio (i.e. below 1) a free binder plateau can be observed, which is ligand concentration and $K_D$-specific, thus, at low binder:ligand ratios a constant value for the free binder fraction is obtained. Likewise, at a high binder:ligand ratio (i.e. above 1) a free ligand plateau can be observed, which is binder concentration and $K_D$-specific, thus, at high binder:ligand ratios a constant value for the free ligand fraction is obtained.

One aspect as reported herein is a method for the determination of the binding affinity ($K_D$ value) of a binder to its ligand comprising the following steps:

determining the fraction of free (i.e. non-complexed) binder, which specifically binds to a ligand, in a sample comprising binder, ligand and non-covalent binder-ligand-complexes in the free binder plateau, and calculating based on the fraction of free (non-complexed) binder determined in the previous step the binding affinity ($K_D$ value) for the binder to its ligand.

One aspect as reported herein is a method for the determination of the binding affinity ($K_D$ value) of a binder to its ligand comprising the following step:

determining the fraction of free (i.e. non-complexed) ligand, which specifically binds to a binder, in a sample comprising binder, ligand and non-covalent binder-ligand-complexes in the free ligand plateau, and calculating based on the fraction of free (non-complexed) ligand determined in the previous step the binding affinity ($K_D$ value) for the ligand to its binder.

One aspect as reported herein is a method for the determination of the binding affinity ($K_D$ value) of a binder to its ligand comprising the following step:

determining the fraction of binder-ligand-complexes in a sample comprising binder, ligand and non-covalent binder-ligand-complexes in the free binder plateau or free ligand plateau, calculating the fraction of free (non-complexed) binder or ligand based on the determined binder-ligand-complexes, and calculating based on the fraction of free (non-complexed) binder or ligand calculated in the previous step the binding affinity ($K_D$ value) for the ligand to its binder.

One aspect as reported herein is a method for the determination of the binding affinity ($K_D$ value) of a binder to its ligand comprising the following step:

determining the fraction of free (i.e. non-complexed) binder, which specifically binds to a ligand, in a sample comprising binder, ligand and non-covalent binder-ligand-complexes for at least two different binder:ligand ratios in the sample, and if the determined fraction of free (non-complexed) binder is not comparable for all used binder:ligand ratios then the binder:ligand ratio in the sample is lowered (i.e. the amount of binder is reduced by constant amount of ligand) and the sample is re-analyzed, or determining the fraction of free (i.e. non-complexed) ligand in a sample comprising a binder, which specifically binds to the ligand, ligand and non-covalent binder-ligand-complexes for at least two different binder:ligand ratios in the sample, and if the determined fraction of free (non-complexed) ligand is not comparable for all used binder:ligand ratios then the binder:ligand ratio in the sample is increased (i.e. the amount of ligand is reduced by constant amount of binder) and the sample is re-analyzed, and calculating based on the fraction of free (non-complexed) binder or calculating based on the fraction of free (non-complexed) ligand determined in the previous step the binding affinity ($K_D$ value) for the binder to its ligand.

In one embodiment the method is not a scatchard analysis.

In one embodiment the method does not require linearization of the data points.

In one embodiment the method does not require the calculation of $EC_{50}$ or $IC_{50}$ values.

In one embodiment two or three different binder:ligand ratios are used.

One aspect as reported herein is a method for the determination of the binding affinity ($K_D$ value) of a binder to its ligand comprising the following steps:

determining the fraction of free (non-complexed) binder
in a sample comprising binder, ligand and binder-
ligand-complexes for a first binder:ligand ratio in the
sample,
whereby the binder:ligand ratio is equal or less than a
binder:ligand ratio for which the determined fraction of
free (non-complexed) binder is comparable for at least
two different binder:ligand ratios,
determining the fraction of free (non-complexed) binder
in a sample comprising binder, ligand and binder-
ligand-complexes for at least a second binder:ligand
ratio in the sample,
whereby the second binder:ligand ratio is different from
the first binder:ligand ratio by increasing or reducing
the amount of ligand in the sample and by maintaining
the amount of binder in the sample,
whereby the fraction of free (non-complexed) binder is
comparable for the binder:ligand ratio with increased or
reduced amount of ligand in the sample for an
increased or reduced amount of binder in the sample,
calculating based on the fraction of free (non-complexed)
binder determined in the previous step the binding
affinity ($K_D$ value) for the binder to its ligand.

One aspect as reported herein is a method for the determination of the binding affinity ($K_D$ value) of a binder to its ligand comprising the following steps:
determining the fraction of free (non-complexed) ligand
in a sample comprising binder, ligand and binder-
ligand-complexes for a first binder:ligand ratio in the
sample,
whereby the binder:ligand ratio is equal or higher than a
binder:ligand ratio for which the determined fraction of
free (non-complexed) ligand is comparable for at least
two different binder:ligand ratios,
determining the fraction of free (non-complexed) ligand
in a sample comprising binder, ligand and binder-
ligand-complexes for at least a second binder:ligand
ratio in the sample,
whereby the second binder:ligand ratio is different from
the first binder:ligand ratio by increasing or reducing
the amount of binder in the sample and by maintaining
the amount of ligand in the sample,
whereby the fraction of free (non-complexed) ligand is
comparable for the binder:ligand ratio with increased or
reduced amount of binder in the sample for an
increased or reduced amount of ligand in the sample,
calculating based on the fraction of free (non-complexed)
ligand determined in the previous step the binding
affinity ($K_D$ value) for the binder to its ligand.

One aspect as reported herein is a method for the determination of the binding affinity ($K_D$ value) of a binder to its ligand comprising the following steps:
determining the fraction of free (non-complexed) binder
in a sample comprising binder, ligand and binder-
ligand-complexes for a first binder:ligand ratio in the
sample,
whereby the binder:ligand ratio is equal or higher than a
binder:ligand ratio for which the determined fraction of
free (non-complexed) ligand is comparable for at least
two different binder:ligand ratios,
determining the fraction of free (non-complexed) binder
in a sample comprising binder, ligand and binder-
ligand-complexes for at least a second binder:ligand
ratio in the sample,
whereby the second binder:ligand ratio is different from
the first binder:ligand ratio by increasing or reducing
the amount of binder in the sample and by maintaining
the amount of ligand in the sample,
whereby the fraction of free (non-complexed) binder is
comparable for the binder:ligand ratio with increased or
reduced amount of binder in the sample for an
increased or reduced amount of ligand in the sample,
calculating based on the fraction of free (non-complexed)
binder determined in the previous step the binding
affinity ($K_D$ value) for the binder to its ligand.

One aspect as reported herein is a method for the determination of the binding affinity ($K_D$ value) of a binder to its ligand comprising the following steps:
determining the fraction of binder-ligand-complex in a
sample comprising binder, ligand and binder-ligand-
complexes for a first binder:ligand ratio in the sample,
whereby the binder:ligand ratio is equal or higher than a
binder:ligand ratio for which the determined fraction of
binder-ligand-complex is comparable for at least two
different binder:ligand ratios,
determining the fraction of binder-ligand-complex in a
sample comprising binder, ligand and binder-ligand-
complexes for at least a second binder:ligand ratio in
the sample,
whereby the second binder:ligand ratio is different from
the first binder:ligand ratio by increasing or reducing
the amount of binder in the sample and by maintaining
the amount of ligand in the sample,
whereby the fraction of binder-ligand-complex is comparable for the binder:ligand ratio with increased or
reduced amount of binder in the sample for an
increased or reduced amount of ligand in the sample,
calculating based on the fraction of binder-ligand-complex determined in the previous step the binding affinity
($K_D$ value) for the binder to its ligand.

One aspect as reported herein is a method for the determination of the binding affinity ($K_D$ value) of a binder to its ligand comprising the following steps:
determining the free binder fraction in at least two
samples with different binder:ligand ratios,
whereby in the at least two samples the amount of
binder is kept constant (is the same) and the amount
of ligand is different in each sample, with the proviso
that the sample comprises excess ligand compared to
binder,
or
determining the free ligand fraction in at least two
samples with different binder:ligand ratios,
whereby in the at least two samples the amount of
ligand is kept constant (is the same) and the amount
of binder is different in each sample, with the proviso
that the sample comprises excess binder compared to
ligand,
calculating based on the fraction of free (non-complexed)
binder or calculating based on the fraction of free
(non-complexed) ligand determined in the previous
step the binding affinity ($K_D$ value) for the binder to its
ligand for each sample,
whereby the binding affinity has been determined if the at
least three $K_D$ values are comparable,
whereby if the at least two $K_D$ values are not comparable
the method is repeated using samples in which either
i) the amount of ligand is reduced at constant amount of
the binder, or
ii) the amount if binder is reduced at constant amount of
the ligand,
compared to the samples used in the previous determination.

In one embodiment of all aspects as reported herein the binder/ligand is selected from the group comprising antigen/antibody, cell/label, drug/target, receptor/receptor ligand, enzyme/enzyme substrate, and complexant/metal ion.

In one embodiment of all aspects as reported herein the binder is selected from the group comprising small molecule drug, biologically active polypeptide, and antibody.

In one embodiment of all aspects as reported herein the antibody is selected from the group comprising full length antibody, antibody fragment, and antibody conjugate.

In one embodiment of all aspects as reported herein the antibody is selected from the group comprising monospecific antibody, bispecific antibody, trispecific antibody, tetraspecific antibody, and hexaspecific antibody.

In one embodiment of all aspects as reported herein the antibody is selected from bivalent antibody, trivalent antibody, tetravalent antibody, and hexavalent antibody.

In one embodiment of all aspects as reported herein the sample comprises serum or plasma.

In one embodiment of all aspects as reported herein the determining is by an immunoassay. In one embodiment the re-analyzing is by the same immunoassay. In one embodiment the immunoassay is a heterogeneous assay.

In one embodiment of all aspects as reported herein the drug/binder is an antibody and the target/ligand is the antigen that is specifically bound by the antibody.

In one embodiment of all aspects as reported herein the binder or the ligand is immobilized on a solid phase.

In one embodiment of all aspects as reported herein for the calculation of the $K_D$ value the following equation is used:

$$K_D = (\text{free drug/binder fraction}) * (\text{target/ligand concentration [nM]})/(1 - \text{free drug/binder fraction}).$$

One aspect as reported herein is the use of a single data point (determined using an appropriate calibration) determined at the free binder plateau for the determination of in solution affinity ($K_D$).

One aspect as reported herein is the use of a method as reported herein for the determination of $K_D$ for the determination of binding kinetics/rate constants ($k_{on}$ and $k_{off}$), by determination of free binder or ligand concentrations in the association or sample dilution induced dissociation phase of binder and ligand.

One aspect as reported herein is the use of a method as reported herein for the determination of in solution binding kinetics/rate constants ($k_{on}$ and $k_{off}$).

One aspect as reported herein is the use of a method as reported herein for the determination of in solution $k_{on}$ values. In this case the $K_D$ value is known.

One aspect as reported herein is the use of a method as reported herein for the determination of in solution $k_{off}$ values.

DETAILED DESCRIPTION OF THE INVENTION

It has been found that the determination of affinity and binding kinetics ($K_D$, rate constant for on- and off-rate) of a binder to its ligand in buffer or serum/plasma samples can be effected with a small number of samples based on the determination of free binder or free ligand whereby the determination should be performed within the linear/constant plateau range of the curve, i.e. at low binder/ligand concentration, no changes in free binder fraction, or likewise at high binder/ligand concentration, no changes in free ligand fraction).

It has been found that at a low binder:ligand ratio a free binder plateau can be observed, which is ligand concentration and $K_D$-specific, thus, at low binder:ligand ratios a constant value for the free binder fraction is obtained. Likewise, at a high binder:ligand ratio a free ligand plateau can be observed, which is binder concentration and $K_D$-specific, thus, at high binder:ligand ratios a constant value for the free ligand fraction is obtained.

Figure 5:
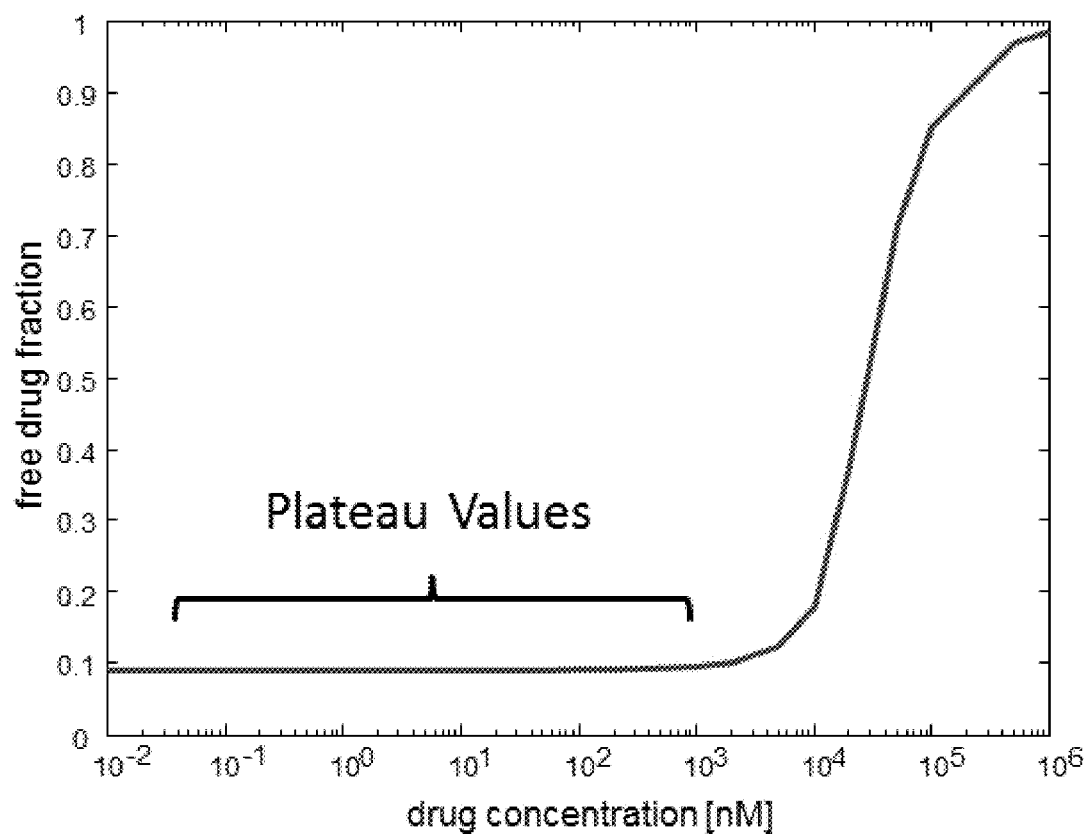
FIG. 5 Exemplary Free Drug/binder concentration curve showing the dependency of free drug/binder fraction by variable total drug/binder concentration.

The term "free binder plateau" denotes the binder concentration range at a constant ligand concentration in samples comprising varying binder concentrations, constant ligand concentrations and respective non-covalent binder-ligand-complexes where the free binder fraction stays constant (see e.g. FIG. 5).

The term "free ligand plateau" denotes the ligand concentration range at a constant binder concentration in samples comprising varying ligand concentrations, constant binder concentrations and respective non-covalent binder-ligand-complexes where the free ligand fraction stays constant.

The term "comparable" denotes that the relative difference (% Diff) of two determined values is less than 100%. In one embodiment the difference is less than 50%. In one embodiment the difference is less than 30%. The difference (% Diff) is calculated with the following formula:

$$\% \text{ Diff} = [(\text{highest value}) - (\text{lowest value})]/(\text{arithmetic mean of the values}).$$

For example, in a first determination 10% free binder has been determined and in a second determination 13% free binder has been determined. According to the formula above this results in a difference of 26% (13−10)/((13+10)/2) =26%).

The term "not-comparable" denotes that the relative difference (% Diff) of two determined values is more than 100%. In one embodiment the difference is more than 50%.

In one embodiment the difference is more than 30%. The difference (% Diff) is calculated with the following formula:

% Diff=[(highest value)−(lowest value)]/(arithmetic mean of the values).

The current invention is exemplified in the following with a drug as example of a binder and a target as example of a ligand. The drug specifically interacts with the target.

Figure 7:
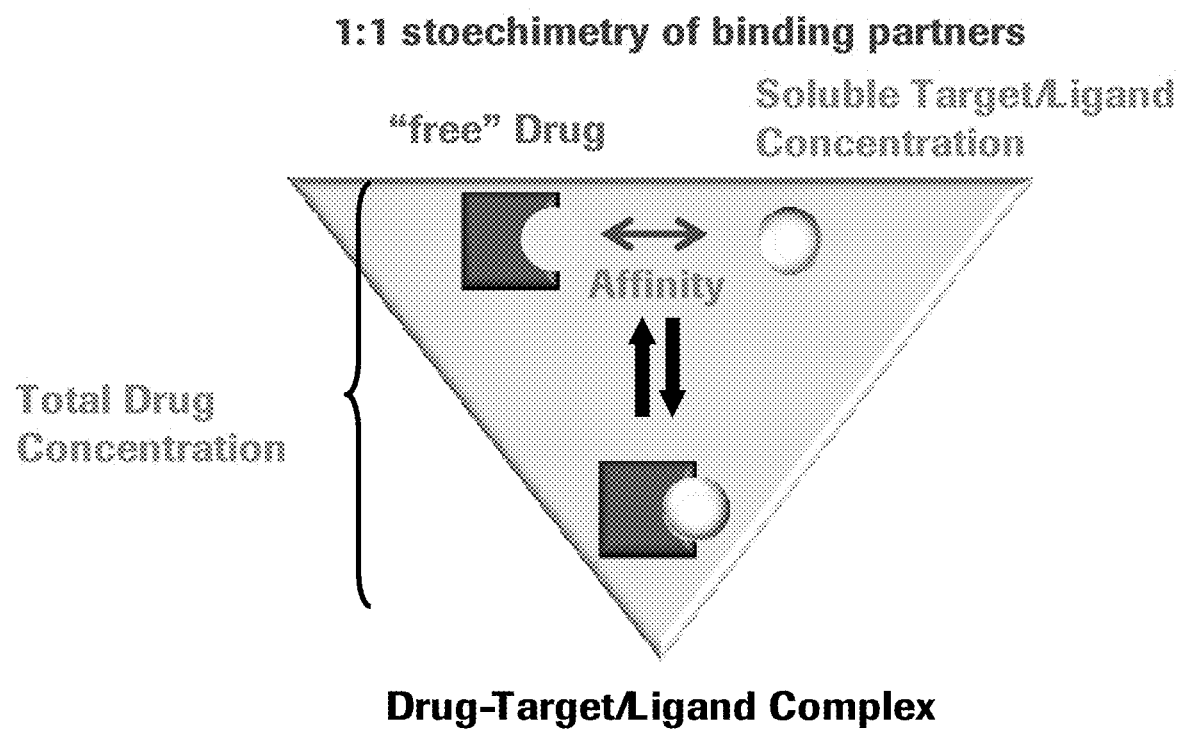
FIG. 7 Mutual dependency between drug/binder concentration, target/ligand concentration and affinity/$K_D$.

As shown in FIG. 7 a mutual dependency between drug concentration, target concentration and affinity ($K_D$) exists.

Figure 8:
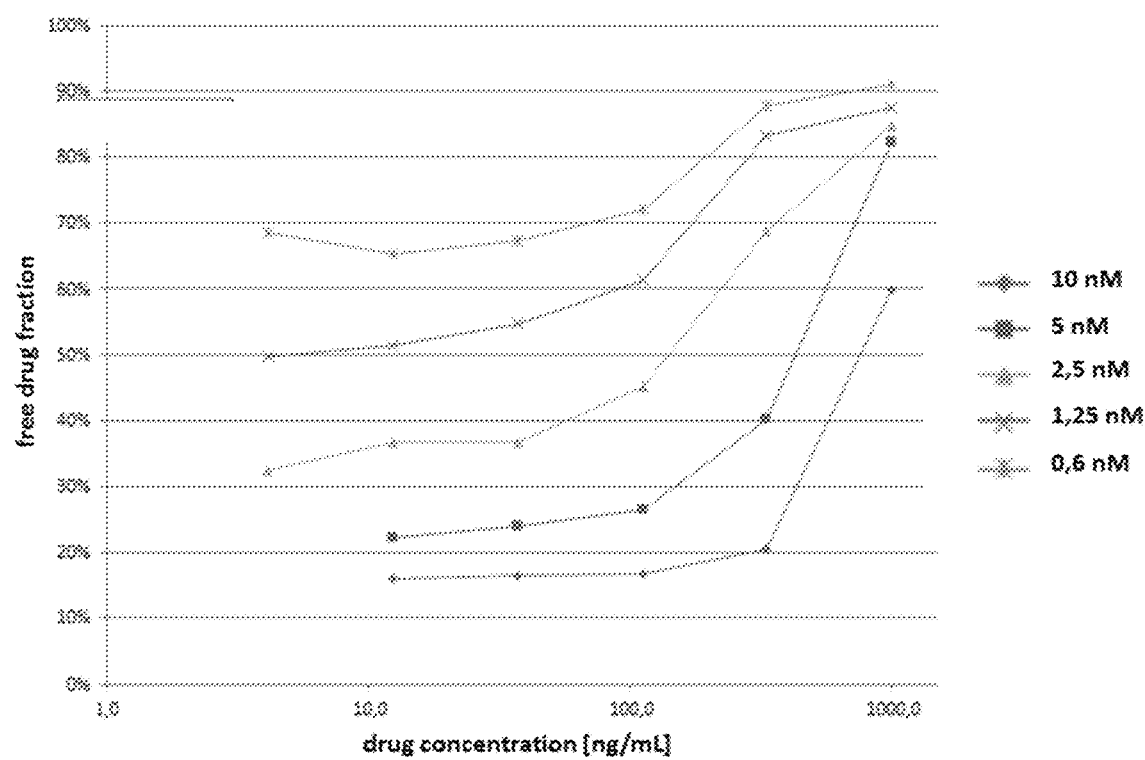
FIG. 8 Free drug/binder fraction depending on drug/binder concentration at constant target/ligand concentration determined for an anti-VEGF antibody as drug/binder and VEGF as target/ligand.

At a low drug:target ratio a free drug plateau can be observed, which is target concentration and $K_D$-specific. An experimentally determined free drug fraction depending on the drug concentration at constant target concentration is shown in FIG. 8. It can be seen that at low drug:target ratios a constant value for the free drug fraction is obtained.

Likewise at high drug:target ratios a similar plateau can be observed. This plateau can also be used for the determination of the $K_D$ value. Therefore, all aspects and embodiment that are directed to a low drug:target ratio (excess of target) can also be performed with a high drug:target ratio (excess of drug).

Likewise the method can be varied by determining the free target concentration if an excess of drug is used. Therefore, all aspects and embodiments that are directed to a drug can also be performed when directed to a target.

Figure 9:
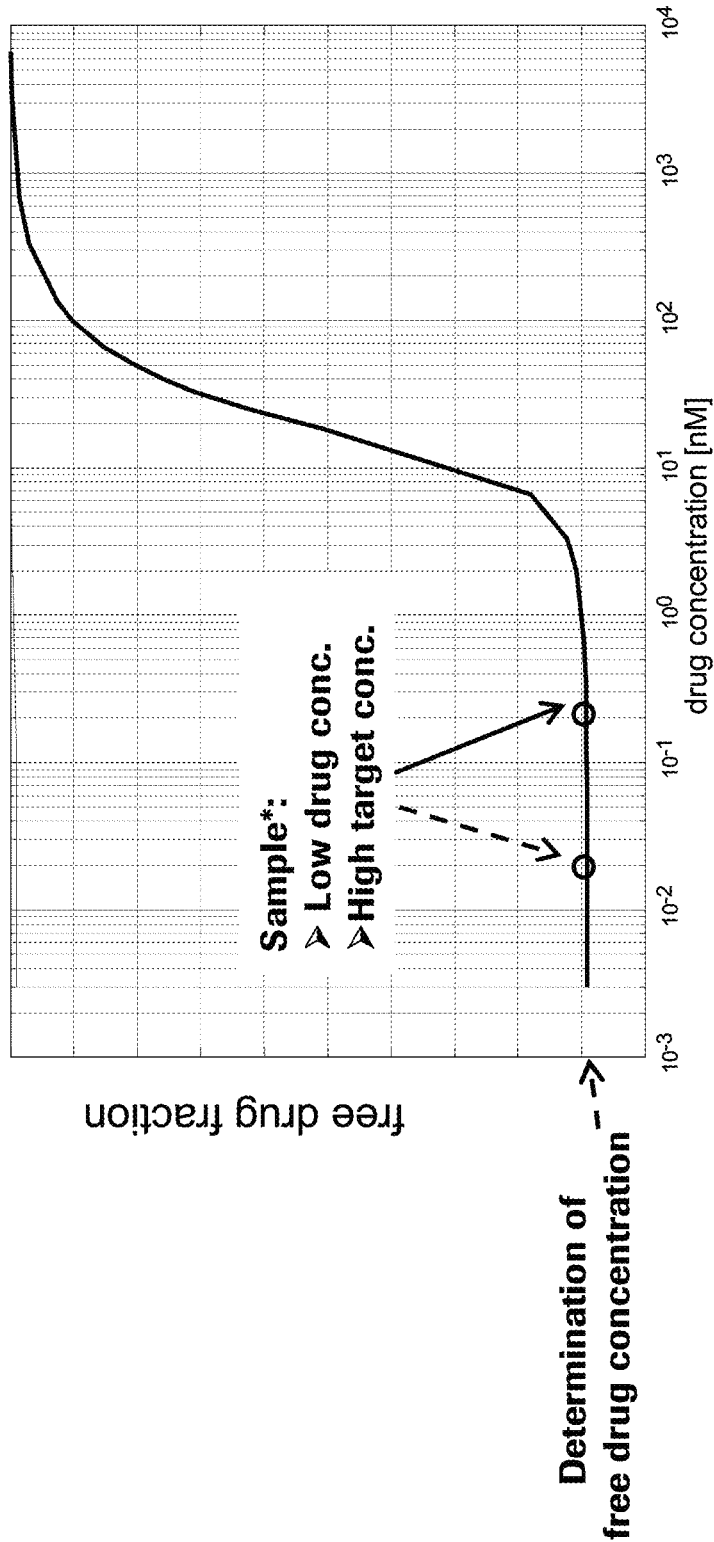
FIG. 9 $K_D$ is constant independent from drug/binder concentration within free drug/binder plateau.

It has been found that the free drug fraction and correspondingly the $K_D$ value is constant independent from drug concentration within the free drug plateau (see FIG. 9).

Figure 10:
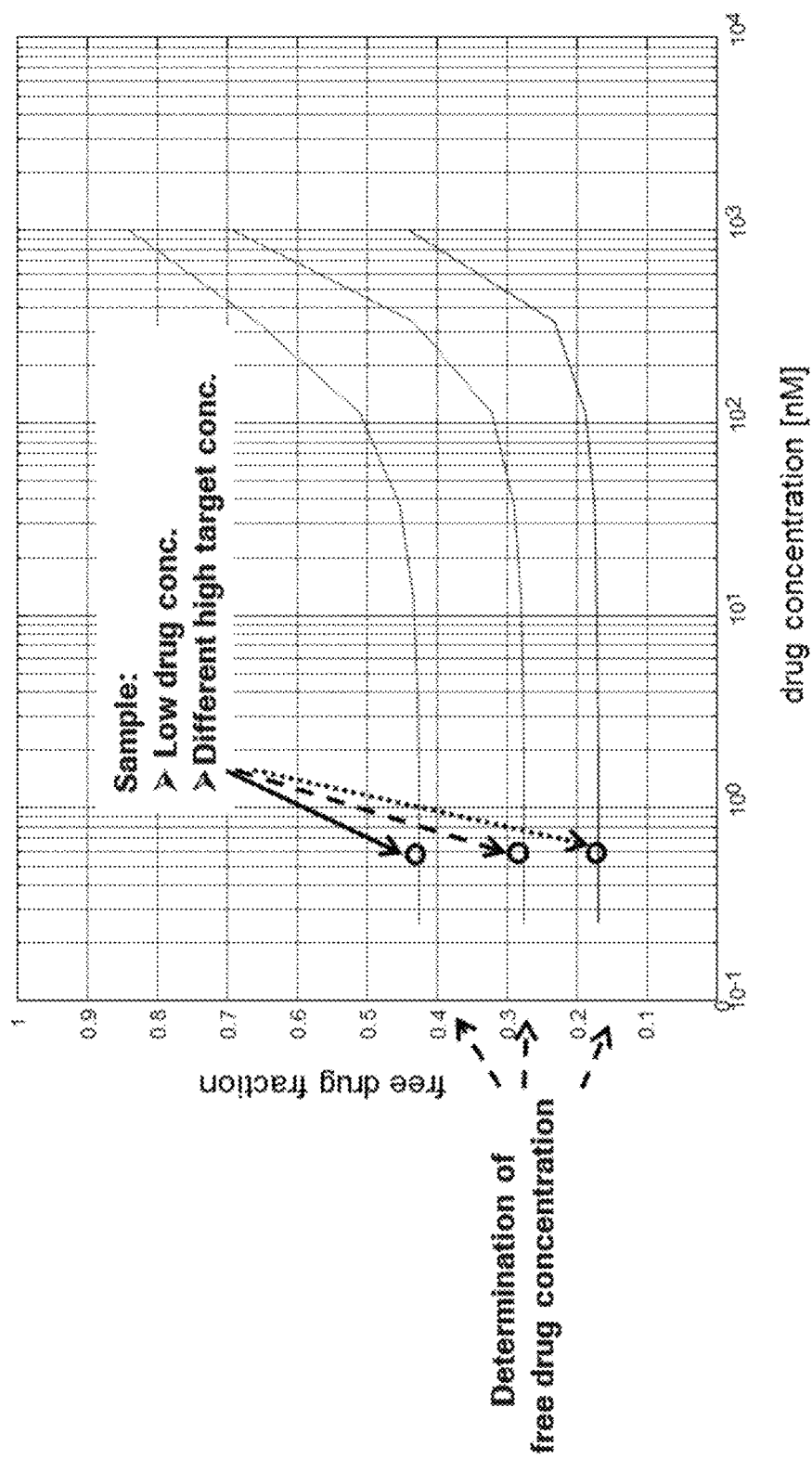
FIG. 10 $K_D$ is constant independent from target/ligand concentration within free drug/binder plateau.

It has been found that the $K_D$ value is constant independent from target concentration within free drug plateau (see FIG. 10).

Figure 1:
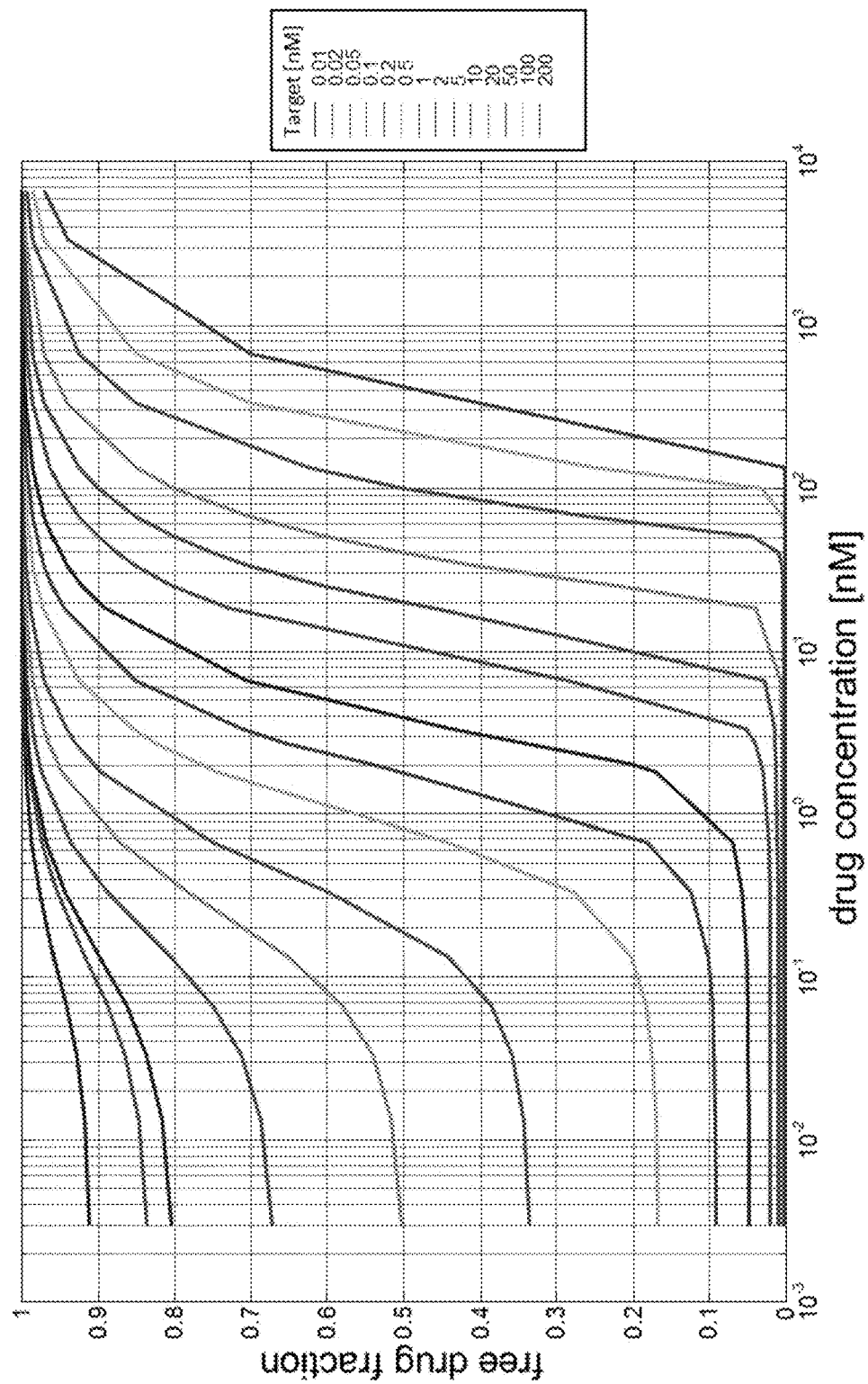
FIG. 1 Dependency of the free drug/binder fraction on variable drug/binder and target/ligand concentrations assuming typically encountered affinities ($K_D$=fixed (0.1 nM ($1 \times 10^{-10}$ M)), target/ligand=variable, drug/binder=variable).

To determine drug-target affinity and binding kinetics ($K_D$, rate constant for on- and off-rate) in buffer or serum/plasma samples, samples were generated with different expected free drug/analyte concentration (for $K_D$ estimation the equilibrium has to be reached). The free drug/analyte fraction has to be in the linear/constant plateau range of the curve (low drug/analyte concentration, no changes in free drug fraction). For a first estimation of the free drug/analyte fraction FIG. 1 gives the corresponding concentrations. The real free drug/analyte fractions were analyzed. The affinity ($K_D$) and rate constants ($k_{on}$, $k_{off}$) were calculated by using the determined free drug fraction.

Thus, any method that is suitable for the determination of free drug fraction can be used in the method as reported herein.

Alternatively the free drug fraction can be determined indirectly by using an assay setup for the determination of the formed complex.

For example, to determine the free drug/analyte concentration in buffer or serum/plasma samples two serial sandwich enzyme linked immunosorbent assays (ELISA) can be used.

Figure 2:
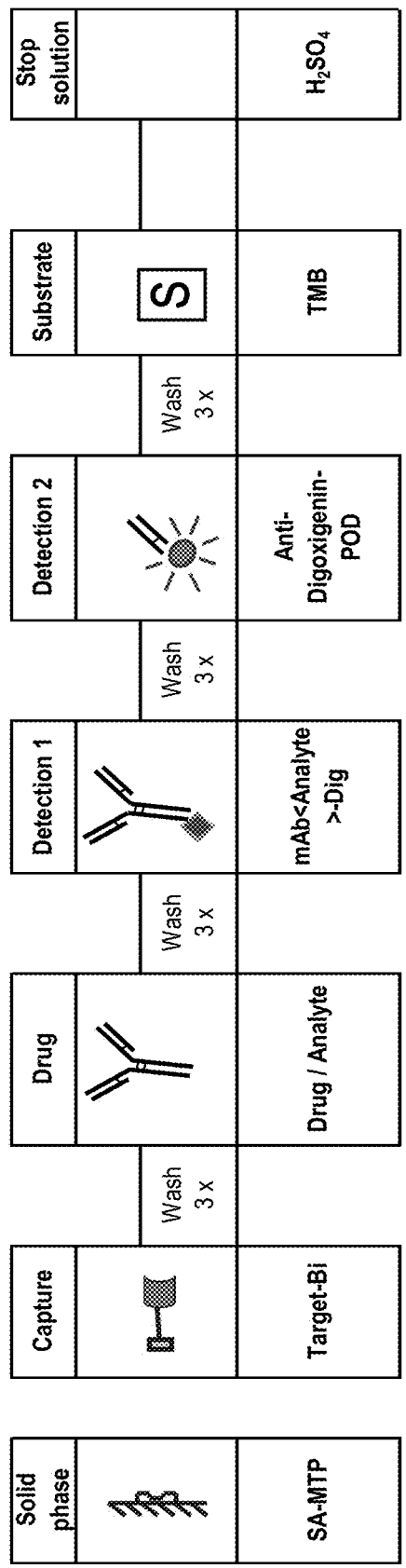
FIG. 2 Schematic description of ELISA test procedure (1).
Figure 3:
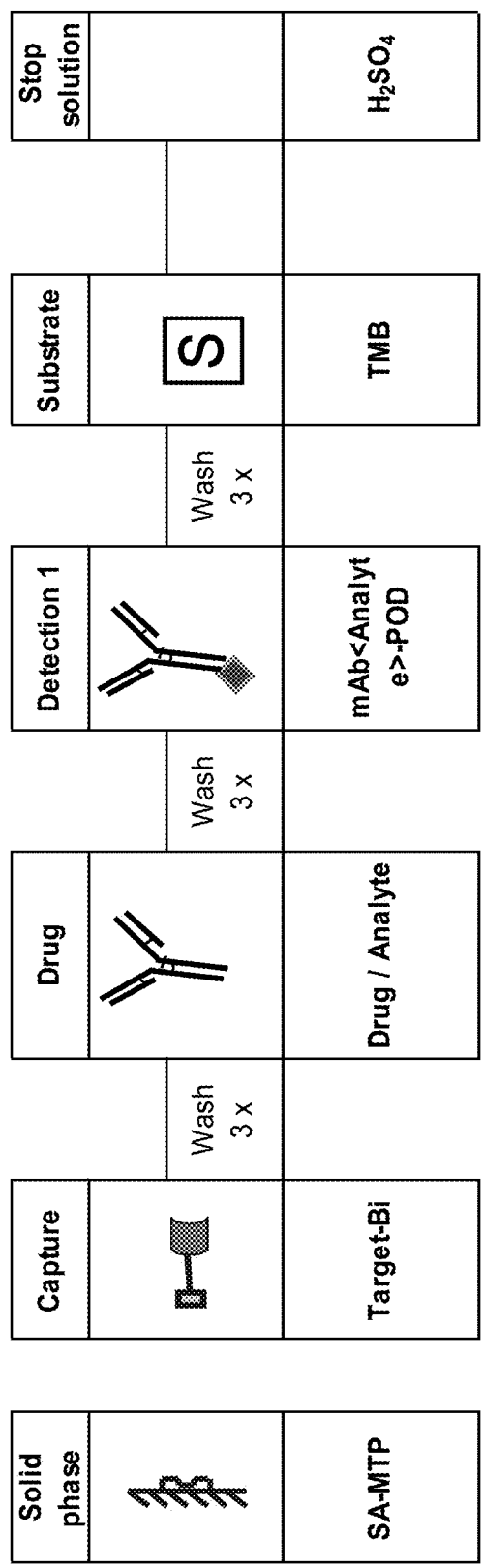
FIG. 3 Schematic description of ELISA test procedure (2).

FIGS. 2 and 3 show the different steps of the ELISA based assay procedure.

In more detail, biotinylated capture protein (target-Bi), drug/analyte, mAb<drug/analyte>-Dig and anti-Digoxigenin-POD are successively added to a streptavidin (SA) coated microtiter plate (MTP), incubating each reagent for 1 hour on a MTP shaker. For an assay speed up alternatively mAb<drug/analyte>-POD can be used instead of the combination of mAb<drug/analyte>-Dig and anti-Digoxigenin-POD.

For an accurate image of the free drug/analyte concentration in solution drug/analyte is incubated for about 5 min. (compromise between signal generation and minimum interference of the equilibrium).

After each step the MTP is washed three times and residual fluids are removed. Finally, the formed immobilized immune complexes are visualized by addition of TMB solution, a POD substrate, which is converted to a colored reaction product. The color development should be photometrically monitored (absorption at 680 nm-450 nm reference wave length) and be stopped by addition of 1 M $H_2SO_4$ when the highest calibrator reaches an OD of 0.65. Finally, the color intensity is photometrically determined (absorption at 450 nm-690 nm reference wave length) and is proportional to the analyte concentration in the serum/plasma/buffer sample. The quantification of drug/analyte is performed by back-calculation of the absorbance values using the corresponding standard curve with a non-linear 4 parameter Wiemer-Rodbard curve fitting function.

After recalculating the free drug concentration of the incubated samples a curve, similar to that shown in FIG. 5 can be plotted. At least two comparable free drug values at the plateau should be obtained (direct quality control of the assay, e.g. oligomerization of target).

For the calculation of the $K_D$ value the following equation is used:

$K_D$=(free drug fraction)*(target concentration [nM])/(1−free drug fraction)

Exemplary calculation (see also Example 3):

target concentration=1 nM=constant drug concentration: 17 ng/mL leads to a free Drug fraction of 9.2% drug concentration: 8.5 ng/mL leads to a free Drug fraction of 7.6% thus, $K_D$=0.1 nM and 0.08 nM

With the method as reported herein a low amount of drug is required and high affinity drugs can be analyzed/characterized.

One aspect as reported herein is the use of the method as reported herein for the determination of the $K_D$ value of bivalent drugs, such as antibodies.

In one embodiment the determination of the $K_D$ value is by dilution induced dissociation of drug target complexes starting from a sample at equilibrium.

The intrinsic problem of all in solution approaches for determining the $K_D$ value of bivalent drugs is the presence of an equilibrium between total free drug (no valency occupied), partial free drug (one valency occupied) and bound drug (both valencies occupied) because the in solution approach is based on the determination of free drug.

Generally a sample used for the determination of the $K_D$ value of a bivalent drug comprises a known amount of drug and target. The readout of a free drug assay is via a free drug calibration curve correlated to an amount of the free drug present in the sample. For bivalent drugs the free drug is a mixture of total free drug and partially free drug whereby the individual fractions thereof are distributed according to a statistical distribution. The actual free drug concentration can be determined using the statistical distribution of total free drug and partially free drug which result in the determined total amount of binding competent drugs.

The method can comprise the following steps:
1) immobilization of target, e.g. coating of capture protein (target-Bi) on streptavidin coated solid phase (e.g. microtiter plate)

2) incubation with samples, QC's and calibrators
3) detection of captured drug with labeled anti-drug antibody, e.g. mAb<drug/analyte>-Dig
4) detection of primary antibody with labeled secondary antibody, e.g. with anti-digoxigenin-POD Furthermore, step 3 and Step 4 can be replaced by incubation with mAb<drug/analyte>-POD.

5) Readout
6) Data analysis

The mean values of each standard and each sample dilution is calculated.

A standard calibration curve is generated by a non-linear 4 parameter fit using a Wiemer-Rodbard function (e.g. by using XLfit):

$$OD = A + \frac{B}{1 + C * X^D}$$

$$X = D\sqrt{\frac{A + B - OD}{C * (OD - A)}}$$

A and B are responsible for signal deviation (approximated start and end of the calibration curve). C and D are responsible for the curve shape.

Reproducible and reliable calculations of test sample dilutions are achieved within a concentration range between 0.033 ng/mL (lower limit of quantification) and 8.0 ng/mL (assay concentrations). Samples are diluted to fit into this range.

Figure 4:
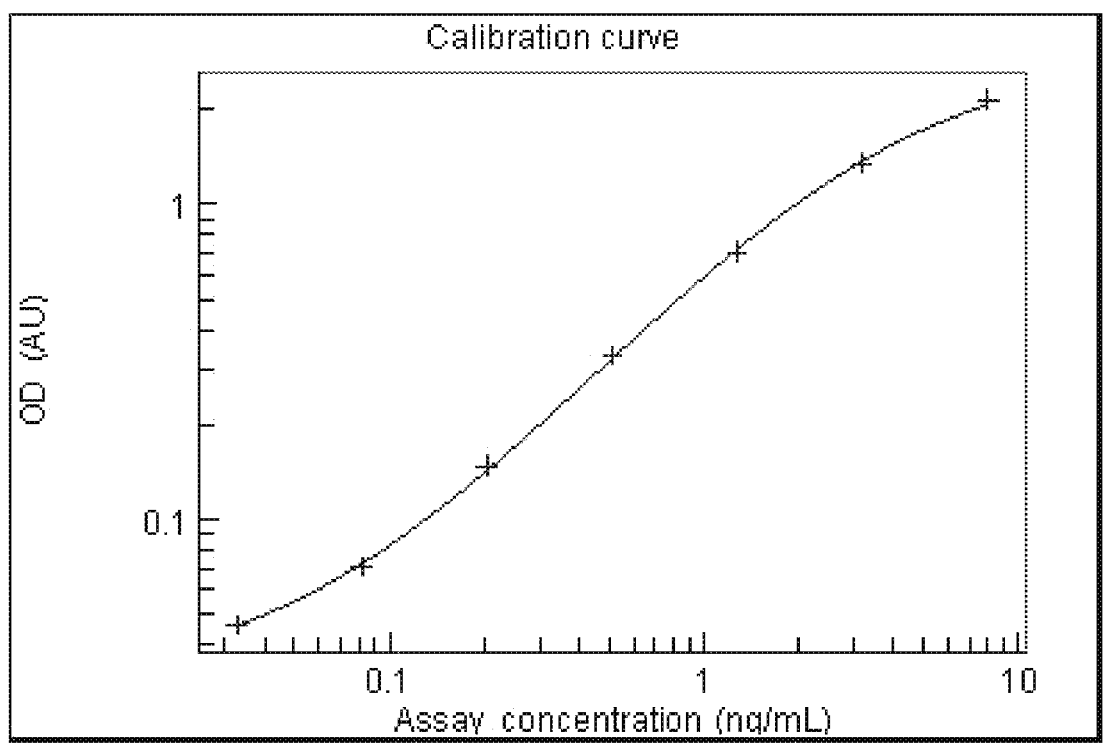
FIG. 4 Assay calibration curve.

A typical calibration curve (calculation with weighting on target concentration) and corresponding data of the assay is shown in FIG. 4.

One aspect as reported herein is the use of the method as reported herein for the determination of the binding kinetics of binders.

This method comprises three steps:
1) sample generation,
2) free drug or free target quantification, and
3) binding kinetic calculation.

In principle two approaches are possible:
a) an association and equilibrium approach, and
b) an equilibrium and dissociation approach by dilution induced dissociation of drug target complexes in a sample starting from equilibrium conditions.

Figure 6:
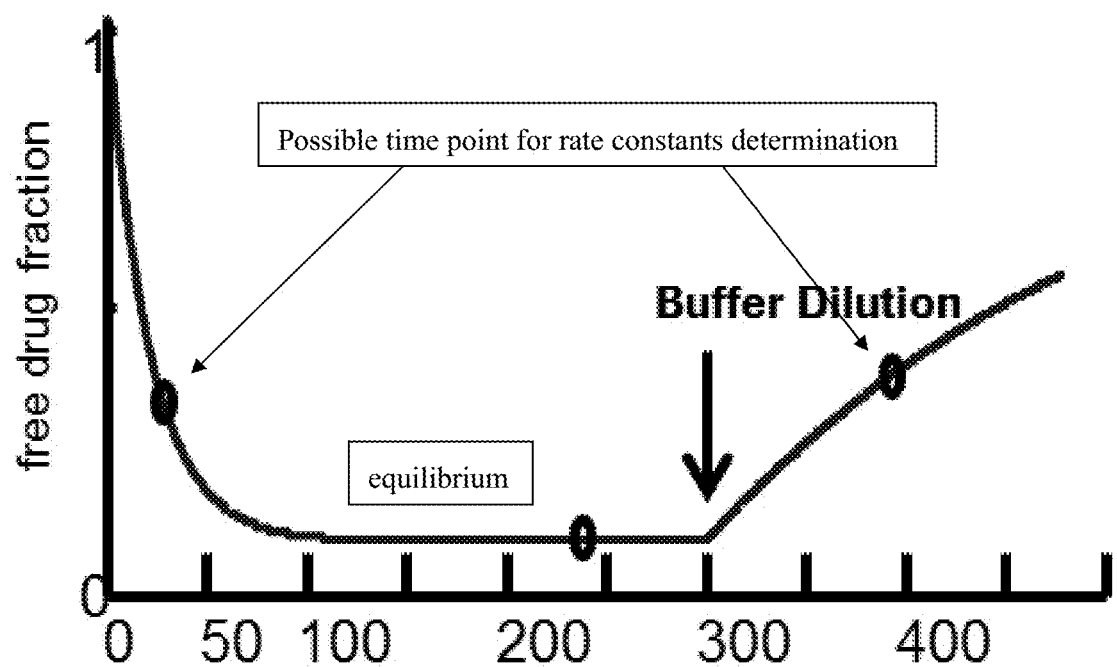
FIG. 6 Dependency of free drug/binder fraction by time and after buffer dilution after reaching equilibrium.

For a given $K_D$ only one $k_{on}$ and $k_{off}$ can result in free drug fractions at two given time points (see FIG. 6).

For the determination of the rate constant of an interaction two methods are possible. For the calculation of the rate constant both methods use the $K_D$ value as a constant which has to be determined. One possible approach is to mix both binding partners and measure during the association phase e.g. free drug fraction ("association-equilibrium approach"). The other possibility for the determination of the rate constant is to perturbate an equilibrated mixture by dilution and measure e.g. the free drug fraction during the dissociation phase before the equilibrium is reached ("equilibrium-dissociation approach"). For each approach only one data point of the not equilibrated sample is necessary. The calculation of the rate constant is performed by solving the differential equations of the system (e.g. reaction $2^{nd}$ order). There is only one pair of $k_{on}$ (rate constant for the association) and $k_{off}$ (rate constant for the dissociation) possible which represents the system with the known $K_D$ value. Application of both approaches can be used for mutual confirmation of the determined kinetic parameters.

For the calculation of the rate constants a fit of the estimated free drug fraction at least at one not equilibrium time point (see FIG. 6) to a calculated solution of the following differential equation can be made. The affinity $(K_D)$ is a mandatory value to have an anchor for calculation. By variation of $k_{on}$ or $k_{off}$ the fit is optimized.

Differential equation:

$$d/dt(\text{drug}) = -k_{on} * \text{drug} * \text{target} + k_{off} * \text{complex}$$

$$d/dt(\text{target}) = -k_{on} * \text{drug} * \text{target} + k_{off} * \text{complex}$$

$$d/dt(\text{complex}) = k_{on} * \text{drug} * \text{target} - k_{off} * \text{complex}$$

For the determination of binding kinetics the immunoassay as reported herein for the determination of free drug can be used.

Figure 11:
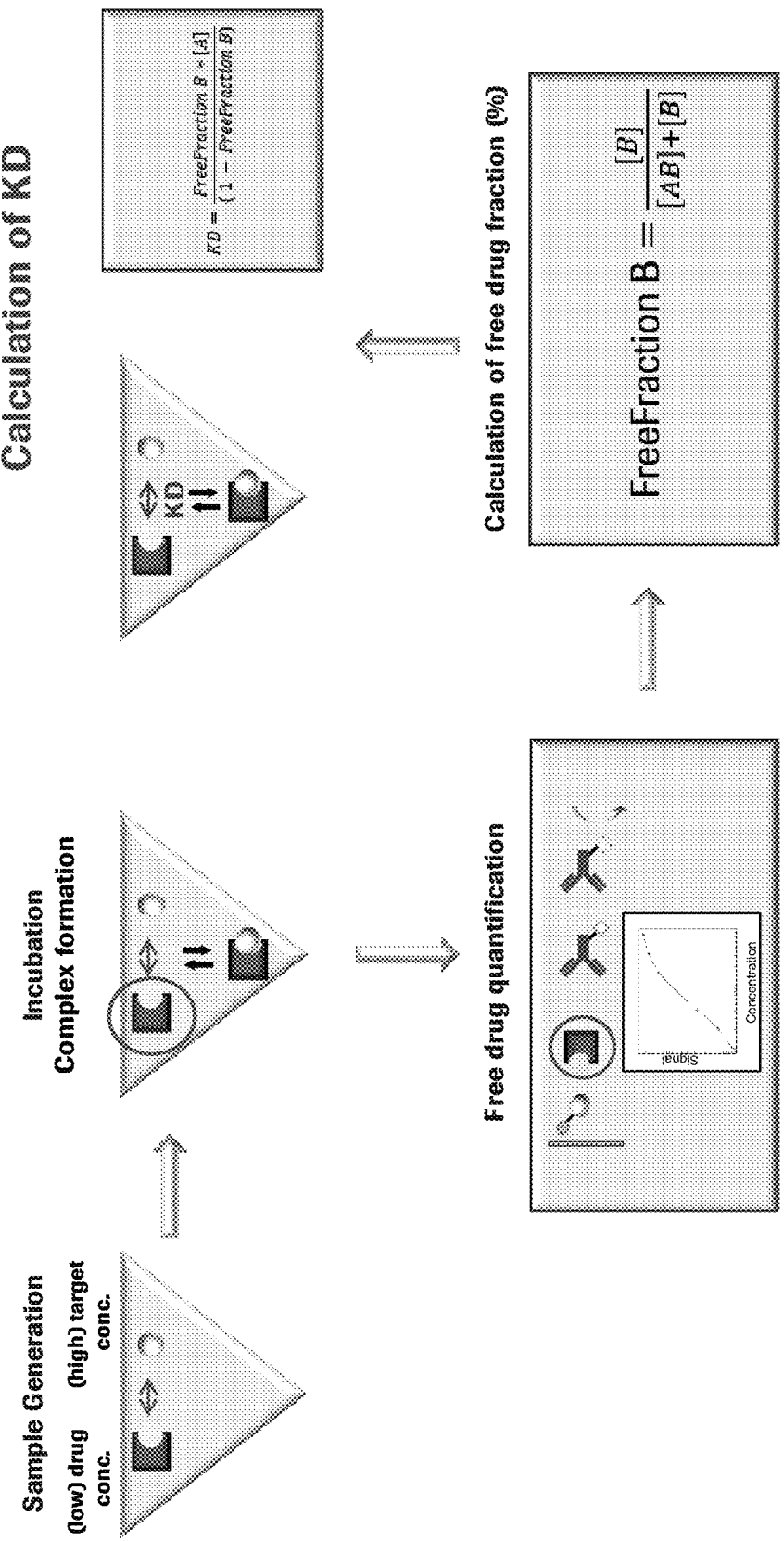
FIG. 11 Schematic description of immunoassay-based binding kinetics determination.

FIG. 11 show the different steps of the assay procedure. The assay comprises the following steps:
1) Sample preparation
   low drug concentration and high target concentration, or
   high drug concentration and low target concentration
2) Incubation and complex formation
3) Free drug quantification or free target quantification see example 2
4) Calculation of free drug fraction or free target concentration $$\text{e.g. } FreeFraction\ B = \frac{[B]}{[AB] + [B]}$$

$$KD = \frac{FreeFraction\ B * [A]}{(1 - FreeFraction\ B)}$$

Thus, the methods as reported herein have characteristic features such as
for the determination of the binding affinity ($K_D$ value)
  i) one partner is present in (large) excess (either drug or target),
  ii) the analysis/determination of two or three samples is sufficient for the determination of the $K_D$ value, and
  iii) most prominent an in-built quality control for checking if the samples are within the plateau region,
for the determination of the binding kinetics ($k_{on}$ and $k_{off}$ value)
  i) determination of binding kinetics using an immunoassay (no requirement of real time analysis),
  ii) the analysis/determination of two samples is sufficient for the determination of the $k_{on}$ and $k_{off}$ values, and
  iii) most prominent using a dilution approach for the determination of binding kinetics (by diluting a sample in which the equilibrium has been reached),
for the determination of the bivalent drugs
  i) most prominent using a statistical approach for the determination of total free and partial free drug in a sample.

The following examples and figures are provided to aid the understanding of the present invention, the true scope of which is set forth in the appended claims. It is understood that modifications can be made in the procedures set forth without departing from the spirit of the invention.

Abbreviations

BLQ Below limit of quantification
BPA 1 Bovine plasma albumin 1
CoA Certificate of analysis
Conc. Concentration
CV Coefficient of variation
Dig Digoxigenin
ELISA Enzyme linked immunosorbent assay
$H_2SO_4$ Sulfuric acid
IgG Immunoglobulin G
mAb Monoclonal antibody
MTP Microtiter plate
OD Optical density
PBS Phosphate buffered saline
POD Polymerized horse-radish peroxidase
QC Quality control
RPM Revolutions per minute
RT Room temperature (+15° C. to +25° C.)
SA Streptavidin
SD Standard deviation
TMB 3,3',5,5'-Tetramethylbenzidine

EXAMPLES

Materials
Equipment
  ELISA—Reader for 96 well MTPs (Monitoring-k: 680/450 nm, Measuring-λ: 450/690 nm)
  Microtiter plate (MTP)—washer
  Microtiter plate (MTP)—shaker
  Standard- and Multi-Pipettes
  Reaction tubes
  General laboratory equipment
Consumables
  Streptavidin coated microtiter plates
  TMB ready-to-use substrate solution
  10×PBS
  Dilute 1:10 in deionized water to 1×PBS.
  Albumin, Bovine Plasma Albumin 1 (BPA 1)
  TWEEN® 20
Samples
  Pool Serum/Plasma of a minimum of 10 healthy untreated human individuals (centrifuge serum samples to avoid pipetting of clotted or turbid serum into MTP wells).
Buffers
  Assay Buffer: 0.5% BPA1 in 1×PBS
  e.g. dilute 5 g BPA1 in 1000 mL 1×PBS
  Washing Buffer: 1×PBS/0.05% TWEEN® 20
  e.g. dilute 10 mL TWEEN® 20 in 2000 mL 1×PBS
  Diluent Pool Serum/Plasma:
  10% blank human Pool Serum diluted in Assay Buffer
  e.g. mix 1 mL Pool Serum with 9 mL Assay Buffer
Reagents
  Anti-Digoxigenin-POD (poly), Fab fragments (<Dig>-POD)
  Second detection reagent
  Lyophilized aliquot of 50 U, reconstitute with 1 mL deionized water to 50 U/ml.

Example 1

General Assay Principle for $K_D$ Value Determination

To determine the free drug/analyte concentration in buffer or serum/plasma samples two serial sandwich enzyme linked immunosorbent assays (ELISA) had been established.

FIGS. 2 and 3 show the different steps of the assay procedure.

Biotinylated capture protein (target-Bi), drug/analyte, mAb<drug/analyte>-Dig and anti-Digoxigenin-POD are successively added to a streptavidin (SA) coated microtiter plate (MTP), incubating each reagent for 1 hour on a MTP shaker. For an assay speed up alternatively mAb<drug/analyte>-POD can be used instead of the combination of mAb<drug/analyte>-Dig and anti-Digoxigenin-POD.

For an accurate image of the free drug/analyte concentration in solution drug/analyte is incubated for about 5 min (compromise between signal generation and minimum interference of the equilibrium).

After each step the MTP is washed three times and residual fluids are removed. Finally, the formed immobilized immune complexes are visualized by addition of TMB solution, a POD substrate, which is converted to a colored reaction product. The color development should be photometrically monitored (absorption at 680 nm-450 nm reference wave length) and be stopped by addition of 1 M $H_2SO_4$ when the highest calibrator reaches an OD of 0.65. Finally, the color intensity is photometrically determined (absorption at 450 nm-690 nm reference wave length) and is proportional to the analyte concentration in the serum/plasma/buffer sample. The quantification of drug/analyte is performed by back-calculation of the absorbance values using the corresponding standard curve with a non-linear 4 parameter Wiemer-Rodbard curve fitting function.

Example 2

Sample Analysis

Samples, quality control samples (QC) and positive control standards are analyzed in assay buffer.

All steps of the test procedure are performed at +15° C. to +25° C. (RT).

The volumes given are calculated for the preparation of a single MTP. If analyzing more than one MTP multiply the volumes indicated below by the number of MTPs. The minimal pipetting volume is 2 µL.

To ensure accurate measurements, all test samples, positive control sample dilutions (standard curve) and quality control samples should be analyzed in duplicate.
Preparation of Calibration Standards and Test Samples:

Prepare serial titrations of the standard of drug/target (mAb<target>) as standard curve comprising 7 different calibrator concentrations and one blank value (serial dilution 1:2.5 in 100% pooled buffer/serum/plasma).

Prepare several test samples (incubation of drug/analyte with target) as estimated by FIG. 1. It is mandatory, that samples for the determination of the affinity reach their equilibrium, at lowest possible drug/analyte concentrations. For the estimation of the rate constants it is mandatory to measure with accurate time scale and not at equilibrium.

The assay comprises the following steps:
1) Coating of capture protein (target-Bi) on streptavidin coated microtiter plates; 1 h incubation followed by 3× wash
   12 mL of the capture reagent working solution target-Bi with a final concentration of e.g. 500 ng/mL was prepared in assay buffer.
   100 µL of the working solution is pipetted into each MTP well. The MTP is covered with an adhesive cover foil and incubate for 1 hour on a MTP shaker (450 rpm). The MTP is washed three times with 300

μL washing buffer per well and residual washing buffer is removed. Thereafter the standards and samples are added.

2) Loading of samples, QC's and calibrators on plate; about 5 min. incubation (as short as possible) followed by 3× wash 100 μL of standards and 100 μL of test sample dilutions are pipetted in duplicates to the designated wells of the MTP. The MTP is covered with an adhesive cover foil and incubate for 1 hour on a MTP-shaker (450 rpm). The MTP is washed three times with 300 μL washing buffer per well and residual washing buffer is removed. Thereafter the first detection antibody is added.

3) Detection with mAb<drug/analyte>-Dig; 1 h incubation followed by 3× wash

For each MTP, 12 mL of the first detection reagent working solution containing mAb<drug/analyte>-Dig at a final concentration of e.g. 500 ng/mL in assay buffer is prepared.

100 μL of the working solution is pipetted into each MTP well. The MTP is covered with an adhesive cover foil and incubate for 1 hour on a MTP-shaker (450 rpm). The MTP is washed three times with 300 μL washing buffer per well and residual washing buffer is removed. Thereafter the second antibody is added 4) Detection with Anti-Digoxigenin-POD; 1 h incubation followed by 3× wash For each MTP 12 mL of the second detection reagent working solution containing <Dig>-POD at a final concentration of 2.5 mU/mL in assay buffer is prepared.

100 μL of this solution is pipetted into each MTP well. The MTP is covered with an adhesive cover foil and incubated for 1 hour on a MTP-shaker (450 rpm). The MTP is washed three times with 300 μL washing buffer per well and residual washing buffer is removed. Thereafter the substrate reagent is added.

Step 3 and Step 4 can be replaced by incubation with mAb<Drug/Analyte>-POD.

5) Readout was done with TMB solution and stopped with $H_2SO_4$ solution. The absorption was monitored until OD680/450 reached 0.65. The absorption measurement was done until OD450/690 reached 1.8-2.2.

100 μL TMB ready-to-use solution is pipetted into each MTP-well. The MTP can be incubated with shaking at 450 rpm with substrate solution. The absorption is monitored several times to achieve an OD680/450 of the highest standard solution (c=8.0 ng/ml) of 0.65. The reaction is stopped with 50 μL 1 M $H_2SO_4$ solution and measure absorption several times to achieve an OD450/690 of the highest standard solution (c=8.0 ng/ml) of 1.8-2.2.

Monitoring wavelength: 680 nm (Reference wavelength: 450 nm)

Measuring wavelength: 450 nm (Reference wavelength: 690 nm)

6) Data analysis

The mean values of each standard and each sample dilution is calculated.

A standard calibration curve is generated by a non-linear 4 parameter fit using a Wiemer-Rodbard function (e.g. by using XLfit):

$$OD = A + \frac{B}{1 + C * X^D}$$

$$X = D\sqrt{\frac{A + B - OD}{C * (OD - A)}}$$

A and B are responsible for signal deviation (approximated start and end of the calibration curve). C and D are responsible for the curve shape.

Reproducible and reliable calculations of test sample dilutions are achieved within a concentration range between 0.033 ng/mL (lower limit of quantification) and 8.0 ng/mL (assay concentrations). Samples are diluted to fit into this range.

A typical calibration curve (calculation with weighting on target concentration) and corresponding data of the assay is shown in FIG. 4 and the following table.

TABLE

| assay concentration [ng/ml] | sample concentration [ng/ml] | average OD [AU] | CV | calculated sample concentration [ng/ml] | recovery [%] |
|---|---|---|---|---|---|
| 8.0 | 80 | 2.198 | 1.2 | 85 | 107 |
| 3.2 | 32 | 1.516 | 1.3 | 32 | 99 |
| 1.3 | 13 | 0.848 | 1.3 | 13 | 99 |
| 0.51 | 5.1 | 0.409 | 1.9 | 5.2 | 101 |
| 0.20 | 2 | 0.179 | 0.8 | 2.0 | 100 |
| 0.082 | 0.82 | 0.085 | 2.5 | 0.82 | 100 |
| 0.033 | 0.33 | 0.048 | 1.5 | 0.33 | 100 |
| 0 | 0 | 0.023 | 3.1 | BLQ | — |

Example 3

Immunoassay-Based In-Solution $K_D$ Value Determination—Monovalent Binding Example Using a Bispecific Anti-EGFR/IGFR Antibody as Drug and EGFR as Target The immunoassay and determination of free drug as well as the calculation of the $K_D$ value have been performed as outlined above.

The $K_D$ determination (using 15 hour incubation time to assure equilibrium) has been performed with varying drug and target concentrations on different days. The results are shown in the following table.

TABLE

| day | drug [ng/ml] | target [nM] | free analyte [%] | calculated $K_D$ value [nM] | average $K_D$ value [nM] |
|---|---|---|---|---|---|
| 1 | 17 | 10 | 1.37 | 0.14 | 0.10 |
| 1 | 17 | 5 | 2.13 | 0.11 | |
| 1 | 17 | 1 | 9.18 | 0.10 | |
| 1 | 8.5 | 10 | 0.45 ** BLQ | — | |
| 1 | 8.5 | 5 | 1.22 | 0.06 | |
| 1 | 8.5 | 1 | 7.55 | 0.08 | |
| 2 | 17 | 10 | 1.05 | 0.11 | 0.11 |
| 2 | 17 | 5 | 1.85 | 0.09 | |
| 2 | 17 | 1 | 9.47 | 0.10 | |
| 2 | 8.5 | 10 | 0.72 ** BLQ | — | |
| 2 | 8.5 | 5 | 2.96 | 0.15 | |
| 2 | 8.5 | 1 | 8.57 | 0.09 | |
| 3 | 7.5 | 1 | 7.90 | 0.09 | 0.11 |
| 3 | 7.5 | 0.5 | 20.73 | 0.13 | |

It can be seen that the $K_D$ value determination is reproducible and independent from drug concentration and from target concentration.

Example 4

Immunoassay-Based In-Solution $K_D$ Value Determination—Monovalent Binding Example Using a Bispecific Anti-EGFR/IGFR Antibody as Drug and IGFR as Target The immunoassay and determination of free drug as well as the calculation of the $K_D$ value have been performed as outlined above.

The $K_D$ determination (using 15 hour incubation time to assure equilibrium) has been performed with varying drug and target concentrations on different days. The results are shown in the following table.

TABLE

| day | drug [ng/ml] | target [nM] | free analyte [%] | calculated $K_D$ value [nM] | average $K_D$ value [nM] |
|---|---|---|---|---|---|
| 1 | 6.8 | 9.7 | 58 | 13.21 | 8.44 |
| 1 | 6.8 | 4.85 | 60 | 7.32 | |
| 1 | 6.8 | 2.43 | 72 | 6.40 | |
| 1 | 3.4 | 9.7 | 51 | 9.98 | |
| 1 | 3.4 | 4.85 | 64 | 8.55 | |
| 1 | 3.4 | 2.43 | 68 | 5.18 | |
| 2 | 6.8 | 10 | 52 | 10.62 | 9.48 |
| 2 | 6.8 | 5 | 55 | 6.12 | |
| 2 | 6.8 | 1 | 82 | 11.71 | |
| 3 | 6.8 | 10 | 62 | 16.56 | 11.21 |
| 3 | 6.8 | 5 | 68 | 10.80 | |
| 3 | 6.8 | 2.5 | 71 | 6.26 | |

Example 5

Immunoassay-Based Binding Kinetics Determination—Association and Equilibrium Approach Using a Bispecific Anti-EGFR/IGFR Antibody as Drug and EGFR as Target The bispecific antibody was used at a concentration of 17 ng/mL. EGFR (target) was used at a concentration of 1 nM. The determined $K_D$ value is 0.09 nM.

The determined free drug fraction after 30 min. incubation time (association phase) was 0.31 (first time point in FIG. 6). The determined free drug fraction after 180 min. incubation time (equilibrium) was 0.09.

Based on these experimental results the binding kinetics parameter $k_{off}$ was calculated to be 0.000073 (1/s) and the binding kinetics parameter $k_{on}$ was calculated to be 7300000 (1/s*nM).

Example 6

Immunoassay-Based Binding Kinetics Determination—Equilibrium and Dissociation Approach Using a Bispecific Anti-EGFR/IGFR Antibody as Drug and IGFR as Target The bispecific antibody was used at a concentration of 680 ng/mL. IGFR (target) was used at a concentration of 200 nM. The determined $K_D$ value is $9.4 \times 10^{-9}$ M.

The determined free drug fraction at equilibrium was 0.07. The determined free drug fraction 15 min. after buffer dilution (dissociation phase) was 0.67.

Based on these experimental results the binding kinetics parameter $k_{off}$ was calculated to be 0.0014854 (1/s) and the binding kinetics parameter $k_{on}$ was calculated to be 158020 (1/s*nM).

The invention claimed is:

1. A method for the determination of the binding affinity ($K_D$ value) of a drug to its target comprising the following steps:

(a)(i) determining the fraction of free drug in at least three samples with different drug:target ratios, each of which samples comprises drug, target and non-covalent drug-target complexes, whereby in the at least three samples the amount of drug is kept constant and the amount of target is different in each sample, with the proviso that the sample comprises an excess of target concentration compared to drug concentration, or determining the free target fraction in at least three samples with different drug:target ratios, whereby in the at least three samples the amount of target is kept constant and the amount of drug is different in each sample, with the proviso that the sample comprises an excess of drug concentration compared to target concentration, wherein said free drug fraction or said free target fraction is determined by an immunoassay;

(a)(ii) calculating based on the fraction of free drug or calculating based on the fraction of free target determined in the previous step the binding affinity of the drug to its target for each of said at least three samples, thereby generating at least three $K_D$ values, wherein for the calculation of the $K_D$ value the following equation is used: $K_D = [(\text{free drug fraction}) \cdot (\text{target concentration [nM]})]/(1 - \text{free drug fraction})$; and (b) determining whether the three $K_D$ values are comparable, wherein the $K_D$ values are comparable if the relative difference of the highest and lowest $K_D$ values is less than 100%, and wherein relative difference is calculated using the following formula: relative difference = [(highest value) − (lowest value)]/(arithmetic mean of the values);

whereby if the at least three $K_D$ values are comparable, the binding affinity is determined, and whereby if the at least three $K_D$ values are not comparable, method steps (a) and (b) are repeated using samples in which either i) the amount of target is reduced at a constant amount of the drug, or ii) the amount of drug is reduced at a constant amount of the target, compared to the samples used in the previous determination.

2. The method according to claim 1, wherein the sample comprises serum or plasma.

3. The method according to claim 1, wherein the drug is an antibody and the target is the antigen that is specifically bound by the antibody.

4. The method according to claim 1, wherein the target is immobilized on a solid phase.

5. The method according to claim 1, whereby in the at least three samples the amount of drug is kept constant and the amount of target is different in each sample, with the proviso that the sample comprises excess of target concentration compared to drug concentration, and wherein the excess target concentration compared to drug concentration is at least 40 times.

6. The method according to claim 1, whereby in the at least three samples the amount of target is kept constant and the amount of drug is different in each sample, with the proviso that the sample comprises excess of drug concentration compared to target concentration, and wherein the excess drug concentration compared to target concentration is at least 40 times.

* * * * *